United States Patent
Takemoto (10) Patent No.: US 9,465,026 B2
(45) Date of Patent: Oct. 11, 2016

(54) APPARATUS FOR MEASURING BLOOD CELLS AND IMMUNITY FROM WHOLE BLOOD

(71) Applicant: HORIBA, Ltd., Kyoto-shi, Kyoto (JP)

(72) Inventor: Kazumasa Takemoto, Kyoto (JP)

(73) Assignee: HORIBA, Ltd., Kyoto-shi (JP)

( * ) Notice: Subject to any disclaimer, the term of this patent is extended or adjusted under 35 U.S.C. 154(b) by 0 days.

(21) Appl. No.: 14/262,330

(22) Filed: Apr. 25, 2014

(65) Prior Publication Data

US 2014/0322802 A1    Oct. 30, 2014

(30) Foreign Application Priority Data

Apr. 26, 2013  (JP) .................................. 2013-093773

(51) Int. Cl.
| | |
|---|---|
| *G01N 33/50* | (2006.01) |
| *G01N 35/10* | (2006.01) |
| *G01N 33/49* | (2006.01) |
| *G01N 15/10* | (2006.01) |

(52) U.S. Cl.
CPC .......... *G01N 33/5094* (2013.01); *G01N 33/49* (2013.01); *G01N 35/1004* (2013.01); *G01N 2015/1006* (2013.01); *G01N 2333/4737* (2013.01)

(58) Field of Classification Search
CPC .. G01N 33/49; G01N 33/5094; G01N 33/53; G01N 35/1004; G01N 2333/47; G01N 2015/1006
See application file for complete search history.

(56) References Cited

U.S. PATENT DOCUMENTS

| | | | |
|---|---|---|---|
| 4,730,631 A | * | 3/1988 | Schwartz ........... G01N 35/1004 134/155 |
| 6,106,778 A | | 8/2000 | Oku et al. |
| 2006/0213257 A1 | * | 9/2006 | Togashi et al. ............. 73/61.55 |

FOREIGN PATENT DOCUMENTS

| | | |
|---|---|---|
| CN | 87106417 A | 5/1988 |
| CN | 1534298 A | 10/2004 |
| CN | 1788198 A | 6/2006 |

(Continued)

OTHER PUBLICATIONS

ISA European Patent Office, Extended European Search Report of EP14166008, Sep. 29, 2014, 9 pages.

(Continued)

*Primary Examiner* — Jill Warden
*Assistant Examiner* — Matthew Krcha
(74) *Attorney, Agent, or Firm* — Alleman Hall McCoy Russell & Tuttle LLP (57) ABSTRACT

In conventional apparatuses for measuring blood cells and immunity from whole blood, the CRP cell is used for the final cleaning of a nozzle, and CRP measurement—cleaning of the CRP cell—final cleaning of nozzle are performed in this order in the CRP cell. In contrast, in the present invention, an exclusive cleaning chamber A for immunity measurement is further provided for the cleaning nozzle after completion of dispensing the specimen and the reagent(s) for CRP measurement to the CRP cell. Thus, a configuration is adapted wherein the outer surface and inner surface of the nozzle are cleaned in the cleaning chamber A for immunity measurement while the immunity measurement is performed in CRP cell. Since the final cleaning of the nozzle is performed in parallel with the CRP measurement, the time conventionally necessary for the final cleaning of the nozzle can be shortened.

4 Claims, 6 Drawing Sheets

(56) References Cited

FOREIGN PATENT DOCUMENTS

| | | |
|---|---|---|
| EP | 0905514 A1 | 3/1999 |
| EP | 1666888 A2 | 6/2006 |
| JP | S58196461 A | 11/1983 |
| JP | S61234356 A | 10/1986 |
| JP | S62251665 A | 11/1987 |
| JP | H01209372 A | 8/1989 |
| JP | H04006468 A | 1/1992 |
| JP | H05040085 A | 2/1993 |
| JP | 07280813 A | 10/1995 |
| JP | H08285861 A | 11/1996 |
| JP | H10096688 A | 4/1998 |
| JP | 11108923 A * | 4/1999 ............. G01N 33/49 |
| JP | 2001289864 A | 10/2001 |
| JP | 3477352 B2 | 12/2003 |
| JP | 2005249585 A | 9/2005 |

OTHER PUBLICATIONS

State Intellectual Property Office of the People's Republic of China, Office Action and Search Report Issued in Application No. 201410171538.9, Aug. 9, 2016, 6 pages.

* cited by examiner

APPARATUS FOR MEASURING BLOOD CELLS AND IMMUNITY FROM WHOLE BLOOD

FIELD OF THE INVENTION

The present invention relates to an apparatus for measuring blood cells and immunity from whole blood, comprising an immunity measuring part that automatically measures the immunity of a blood specimen, and a blood cell counting-measuring part that automatically performs counting and measurement of blood cells such as classification, counting and the like of the blood cells.

BACKGROUND OF THE INVENTION

When an inflammatory reaction or tissue destruction has occurred in the body, it is diagnosed based on the detection of what is called an inflammation marker as an index. One representative example of the marker is a C-reactive protein (hereinafter to be referred to as CRP). CRP is a serum protein secreted by the liver into the blood on affliction with autoimmune diseases such as rheumatoid arthritis and the like, malignant tumor, primarily bacterial infectious diseases and the like. Therefore, CRP is known to show high values in patients with these diseases.

However, since CRP values show high individual differences, it is a particularly useful index when progression of the disease state of individual patients is observed, rather than comparison with the standard value or CRP values of others. CRP is generally measured immunologically by a method such as ELISA (Enzyme-Linked ImmunoSorbent Assay) and the like.

In the meantime, the shift to the left of white blood cells and an increase in the number of white blood cells occur in early stages of inflammation. Therefore, it is clinically highly important to simultaneously measure not only CRP but also white blood cells.

The present inventors took note of the above-mentioned aspect, provided for the first time an apparatus for measuring blood cells and immunity from whole blood, which simultaneously enables measurement of blood cells including white blood cells and CRP (JP-B-3477352, hereinafter to be referred to as patent document 1).

The apparatus described in patent document 1 is configured to classify white blood cells into 3 types. White blood cells can be divided into five kinds of cells: neutrophil, eosinophil, basophil, monocyte and lymphocyte. Of these, neutrophil, eosinophil and basophil are sometimes referred to collectively as granulocytes. In the apparatus for measuring blood cells and immunity from whole blood of the above-mentioned patent document 1, granulocytes, monocytes and lymphocytes are counted as white blood cells (i.e., classification into 3 types).

Figure 4A:
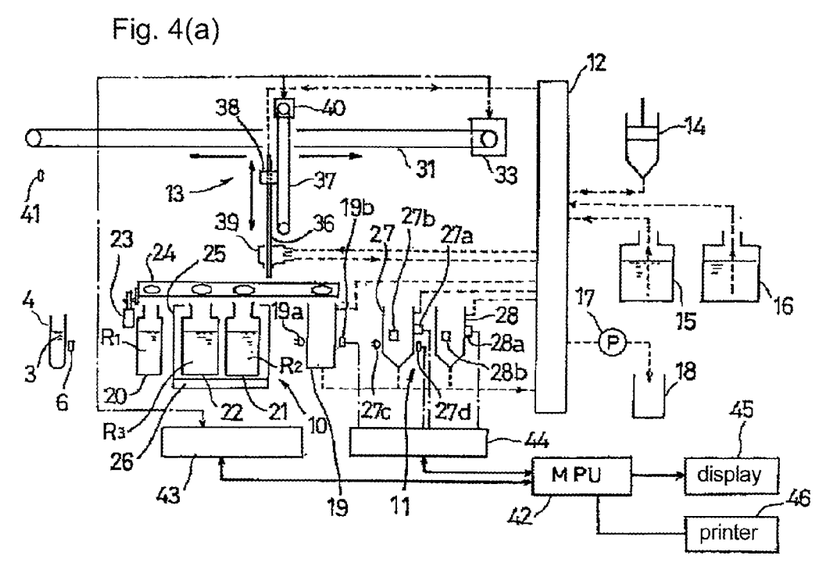
FIGS. 4(a) and 4(b) show the configuration of the apparatus described in patent document 1.
Figure 4B:
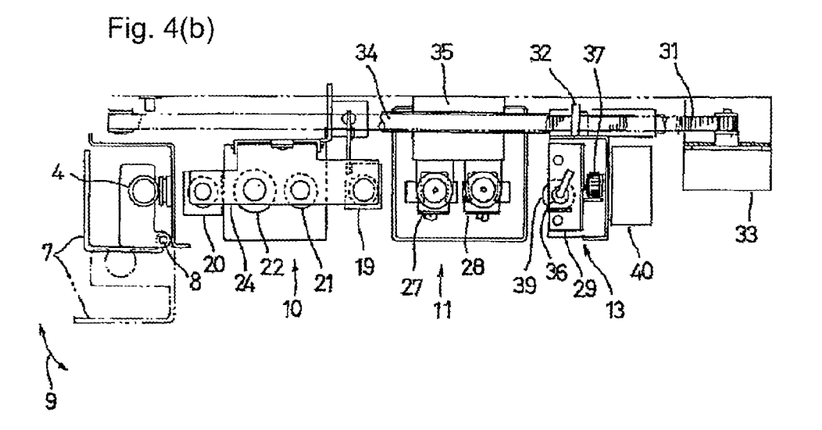
Figure 5:
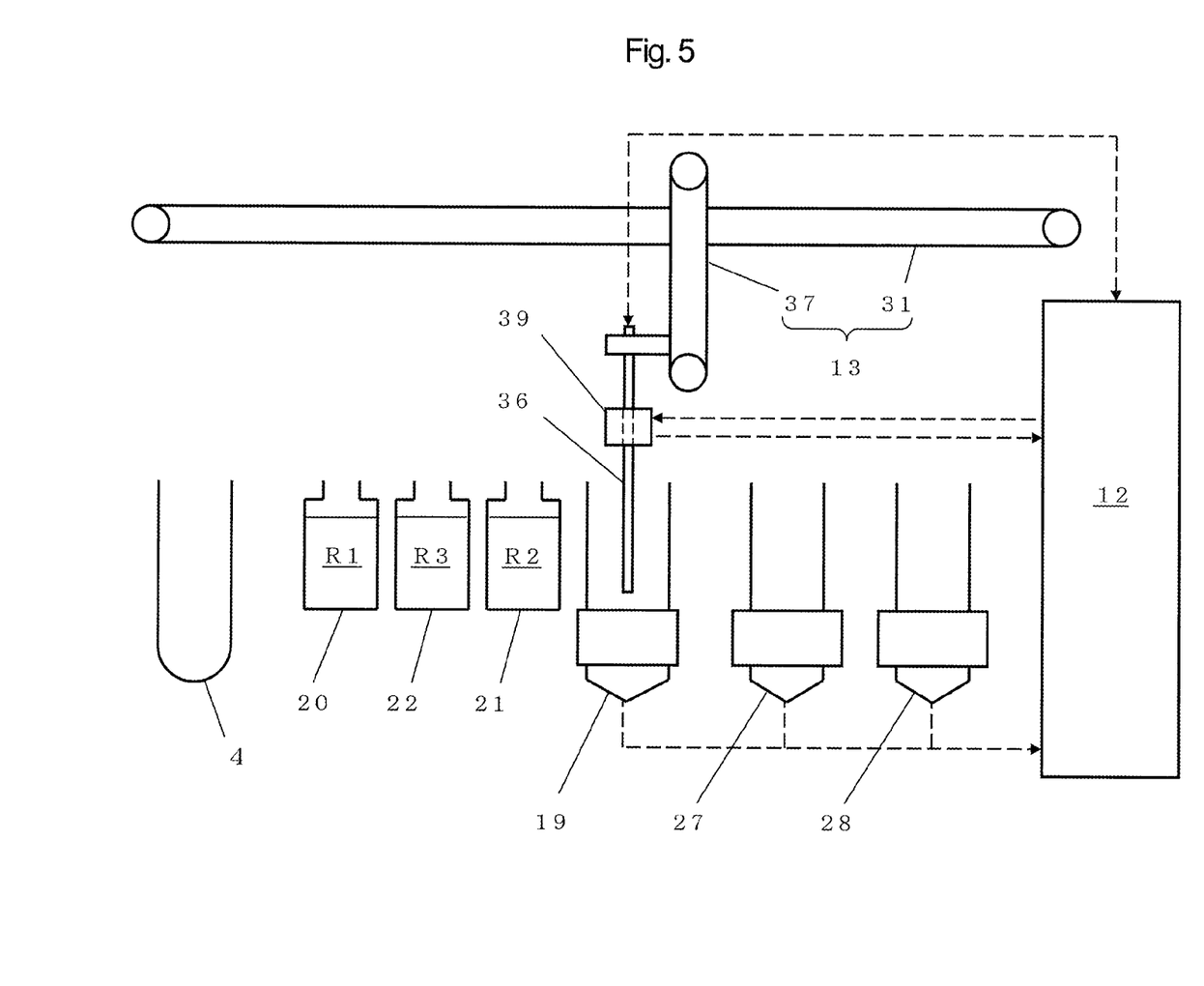
FIG. 5 schematically shows the configuration of the main part of the apparatus of patent document 1 shown in FIG. 4(a).

In the apparatus for measuring blood cells and immunity from whole blood of the above-mentioned patent document 1, a sampling nozzle (being a long and thin pipe, it is also called a "needle") 36 is formed to execute processing steps essential for the CRP measurement (FIGS. 4(*a*), 4(*b*), and FIG. 5).

As shown in FIGS. 4(*a*), (*b*), a specimen container 4 containing a specimen, a CRP cell 19, reagent containers (20, 21, 22) containing the reagents for CRP measurement, and blood cell counting-measuring cells (WBC cell 27 for white blood cell, RBC cell 28 for red blood cell) are aligned and disposed in a line in the horizontal direction. A single sampling nozzle 36 is controlled to move in the horizontal direction (positioning movement above each container and cells) and downward and upward movements (movements to go into and out from each container and cells) in a predetermined order. By these configurations, suction and discharging of specimen and reagents, CRP measurement in the CRP cell, and blood cell counting and measurement in the WBC cell and RBC cell are performed full-automatically.

In the aforementioned apparatus, various processing steps, such as steps of [suction and discharging of specimen and CRP reagents, CRP measurement in CRP cell, blood cell counting and measurement in the WBC cell and RBC cell, cleaning processing of each cell, cleaning processing of the outside of nozzle where necessary after each processing step, and final cleaning processing of the inside and outside of nozzle after the final step] are performed sequentially and full-automatically, and the whole processing steps require about 4 minutes per one specimen to complete.

The processing time of about 4 minutes per one specimen as mentioned above is free of problems and preferable for general tests. However, in an institution where a large number of specimens need to be processed in one day, shortening of time even by several dozen seconds greatly contributes to an increase in the daily through-put.

On the contrary, in conventional apparatuses for measuring blood cells and immunity from whole blood, the moving speed and sucking and discharging speed of the sampling nozzle are appropriate, and each processing step is essential, and therefore, there was no room for reduction in reaction time of reagents, measurement time, cleaning frequency and the like.

The problem of the present invention is to provide an apparatus for measuring blood cells and immunity from whole blood, which is capable of shortening the measurement processing time necessary for one specimen.

SUMMARY OF THE INVENTION

The present invention has the following characteristics.
(1) An apparatus for measuring blood cells and immunity from whole blood, comprising: an immunity measuring part comprising an immunity measuring cell; reagent container(s) containing reagent(s) for the immunity measurement; and a blood cell counting-measuring part comprising blood cell counting-measuring cell(s);

wherein the immunity measuring part, the reagent container(s) and the immunity measuring part are placed at predetermined positions, and wherein the apparatus is configured such that a single sampling nozzle moves to the predetermined positions and moves downwardly and upwardly to suck and discharge a specimen and the reagent(s), and an immunity measurement in the immunity measuring cell and counting and measuring of the blood cells in the blood cell counting-measuring cell(s) are performed, the apparatus further comprising: a cleaning chamber for immunity measurement exclusively for finally cleaning the sampling nozzle after completion of dispensing the specimen and the reagent(s) to the immunity measuring cell(s); and a control configuration such that an outer surface and an inner surface of the sampling nozzle are cleaned in the cleaning chamber for immunity measurement, while the immunity measurement in the immunity measuring cell is performed.

(2) The apparatus for measuring blood cells and immunity from whole blood of the above-mentioned (1), further comprising:

a sampling nozzle cleaning device accompanying the sampling nozzle, which is configured to clean the outer surface of the nozzle with a diluting liquid; and a control configuration such that, in a step for dispensing reagent(s) for immunity measurement to the immunity measuring cell, the outer surface of the sampling nozzle is cleaned by the sampling nozzle cleaning device utilizing the cleaning chamber for immunity measurement.

(3) The apparatus for measuring blood cells and immunity of whole blood of the above-mentioned (1) or (2), further comprising a specimen cleaning chamber; and a control configuration such that the sampling nozzle, which is in a state possibly having blood thereon after dispensing for counting and measurement of the blood cells, is cleaned in the specimen cleaning chamber.

BRIEF DESCRIPTION OF THE DRAWINGS

FIG. 4(a) is FIG. 2 of this document, and FIG. 4(b) is FIG. 3 of this document.

DETAILED DESCRIPTION OF THE INVENTION

In the apparatus for measuring blood cells and immunity from whole blood described in the above-mentioned patent document 1, a sampling nozzle-cleaning device, which is configured to clean the outer surface of the sampling nozzle with a diluting liquid, accompanies the sampling nozzle, as shown in FIGS. 4(a), 4(b), and FIG. 5. The outer surface of the sampling nozzle 36 is cleaned in each step as necessary. For cleaning, the cell in the blood cell counting-measuring part (particularly, WBC cell 27 for white blood cell measurement) is used. That is, the WBC cell 27 also functions as a waste liquid chamber (funnel-like opening) for receiving a waste liquid and a diluting liquid from the nozzle cleaning device. The aforementioned waste liquid and the like are transferred from a discharge port at the bottom of the WBC cell through a piping into the final waste liquid container (18 in FIG. 4(a)).

While the above-mentioned patent document 1 does not explicitly state, conventionally, the sampling nozzle with a latex immunity reagent adhered thereto after completion of all CRP measurements is finally cleaned (sufficient cleaning including cleaning of the inner surface of the nozzle: hereinafter to be also referred to as "final cleaning of nozzle") in the CRP cell 19 rather than the WBC cell 27.

Conventionally, the CRP cell is used for the final nozzle cleaning to avoid contamination of specimens.

Among the three cells (CRP cell 19, WBC cell 27, RBC cell 28), the CRP cell has the least possibility of blood cells remaining. Since a specimen after lysis of all blood cells with a hemolysis reagent R1 is fed into the CRP cell, the possibility of the blood cells remaining therein is close to none. On the contrary, red blood cells may remain in the RBC cell, and not only white blood cells but also red blood cells may remain in the WBC cell also serving as a waste liquid chamber.

Figure 6:
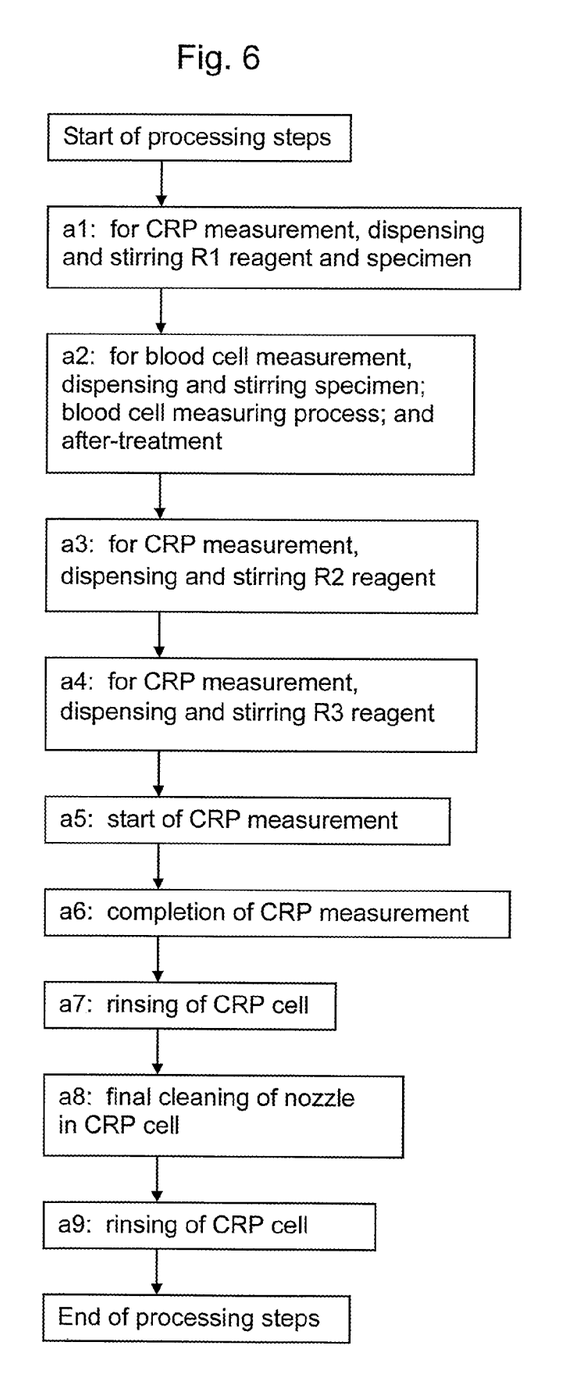
FIG. 6 is a flow chart showing the movement of the sampling nozzle in the apparatus shown in FIG. 4(a).

Therefore, in the apparatus of the above-mentioned patent document 1, the nozzle is finally cleaned after washing the inside of the CRP cell with a diluting liquid after completion of the CRP measurement. This step is as shown in the flow chart of FIG. 6 as steps a6-a8, where the CRP measurement and the final nozzle cleaning are serially performed.

In view of the apparatus for measuring blood cells and immunity from whole blood of the above-mentioned patent document 1, an apparatus added with exclusive measuring-cells has been further developed to enable classification of white blood cells into 5 types. However, even in such an immunity measuring apparatus, final nozzle cleaning requires repeats of discharging and sucking and discharging of a clean diluting liquid into and from the CRP cell and, where necessary, the diluting liquid is discarded and a fresh diluting liquid needs to be used for the above repeats. The cleaning takes about 60 seconds.

In contrast to the above-mentioned conventional steps, the present invention took note of the long time necessary for the CRP measurement itself and the final nozzle cleaning. A configuration is newly employed to have an exclusive chamber for the final nozzle cleaning (cleaning chamber for immunity measurement), wherein the final nozzle cleaning simultaneously proceeds in the cleaning chamber while the CRP measurement is being performed in the CRP cell.

This configuration for simultaneous progress omits about 60 seconds necessary for the final nozzle cleaning, and the processing time for one specimen becomes about 3 minutes from the conventional 4 minutes or so.

Moreover, since a cleaning chamber for immunity measurement has been provided, not only the final nozzle cleaning, but also the outer surface of the sampling nozzle can be cleaned as appropriate after suction of various reagents relating to the immunity measurement, by using the cleaning chamber for immunity measurement. As a result, the risk of contamination of the WBC cell and the measuring part with the reagents for CRP measurement (contamination of WBC measurement sample with reagent for CRP measurement) can be avoided when compared to the conventional cleaning using the WBC cell.

The configuration of the apparatus for measuring blood cells and immunity from whole blood of the present invention is explained in more detail in the following by referring to the Examples.

Figure 1:
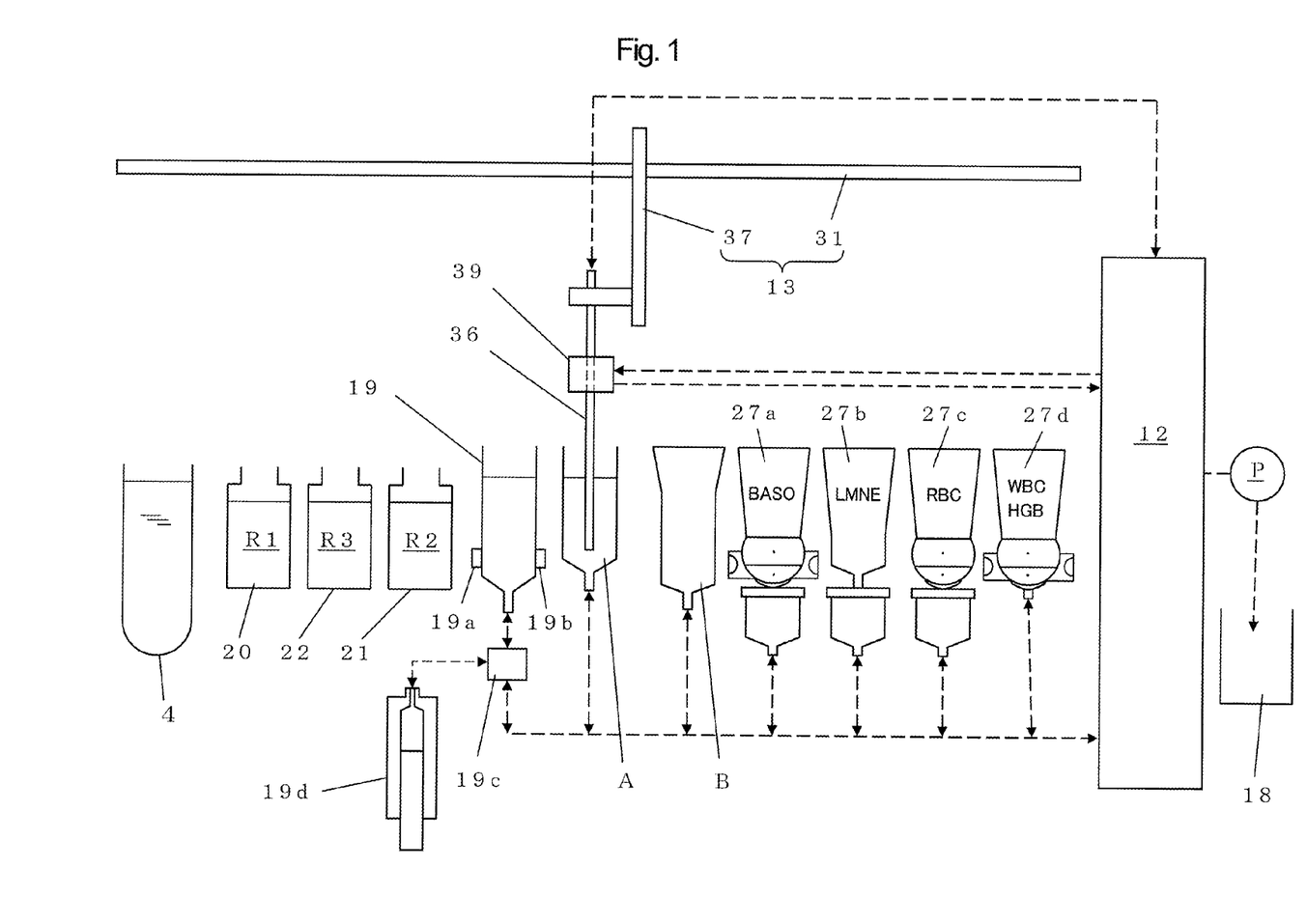
FIG. 1 schematically shows a configuration example of the main part of a preferable embodiment of the apparatus for measuring blood cells and immunity from whole blood of the present invention.

FIG. 1 is partially-enlarged view showing the characteristic configuration part in a preferable embodiment of the apparatus for measuring blood cells and immunity from whole blood of the present invention. As shown in the Figure, the apparatus comprises an immunity measuring part containing an immunity measurement cell 19, reagent containers (20, 21, 22) containing reagents for immunity measurement (R1, R2, R3), respectively, and a blood cell counting-measuring part containing blood cell counting-measuring cells (BASO cell 27a, LMNE cell 27b, RBC cell 27c, WBC cell 27d), in which blood cell counting, hemoglobin concentration measurement and the like are performed, which are disposed at predetermined positions. These measuring-cells form an embodiment preferable for detail analyses including classification of white blood cells into 5 types. These measuring-cells are explained later.

In the embodiment of FIG. 1, a specimen container 4 containing a specimen is set at a predetermined position in the apparatus, and the predetermined positions of the specimen container 4, reagent containers (20, 22, 21), immunity-measuring cell 19 and blood cell counting-measuring cells (BASO cell 27a, LMNE cell 27b, RBC cell 27c, WBC cell 27d) are aligned along a straight line extending in the horizontal direction. A single sampling nozzle 36, that moves in the horizontal direction and the vertical direction by the action of a probe unit 13, moves along the straight line or downwardly or upwardly to enter into or go out from each container and each cell, along which to suck or discharge the specimen or reagent. Such an operating configuration is controlled by a computer. It is configured so that the immunity measurement is automatically performed by the immunity-measuring cell 19 and the control part (not shown), and the counting and measurement of blood cells are automatically performed by the above-mentioned blood cell counting-measuring cells and the control part.

The important characteristic of the present invention is, as shown in FIG. 1, the further addition of the cleaning chamber A for immunity measurement. The cleaning chamber A for immunity measurement is a chamber for exclusively cleaning the sampling nozzle 36 after completion of dispensation of a specimen and reagents for immunity measurement to the immunity-measuring cell 19. The sampling nozzle 36 is controlled by a computer to be cleaned on the outer surface and the inner surface thereof in the cleaning chamber for immunity measurement, while the immunity measurement is being performed in the immunity-measuring cell 19.

While each cell and containers such as a chamber and the like depicted in FIG. 1 have a corner in the bottom, actually, they preferably have appropriate roundness in consideration of the smooth outflow and inflow of the liquid.

The measurement processing time can be drastically shortened by the addition of the cleaning chamber A for immunity measurement and use thereof (final cleaning of the nozzle that simultaneously proceeds with the immunity measurement). In addition thereto, cleaning of a sampling nozzle having blood (particularly blood cells) thereon can be completely separated from the cleaning of a sampling nozzle having a liquid thereon, which liquid containing no residual blood (particularly blood cells) since it was mixed with a hemolysis reagent for immunity measurement. Thus, performing the final cleaning in the cleaning chamber A for immunity measurement, contamination with other specimens can be eliminated more completely.

Figure 3:
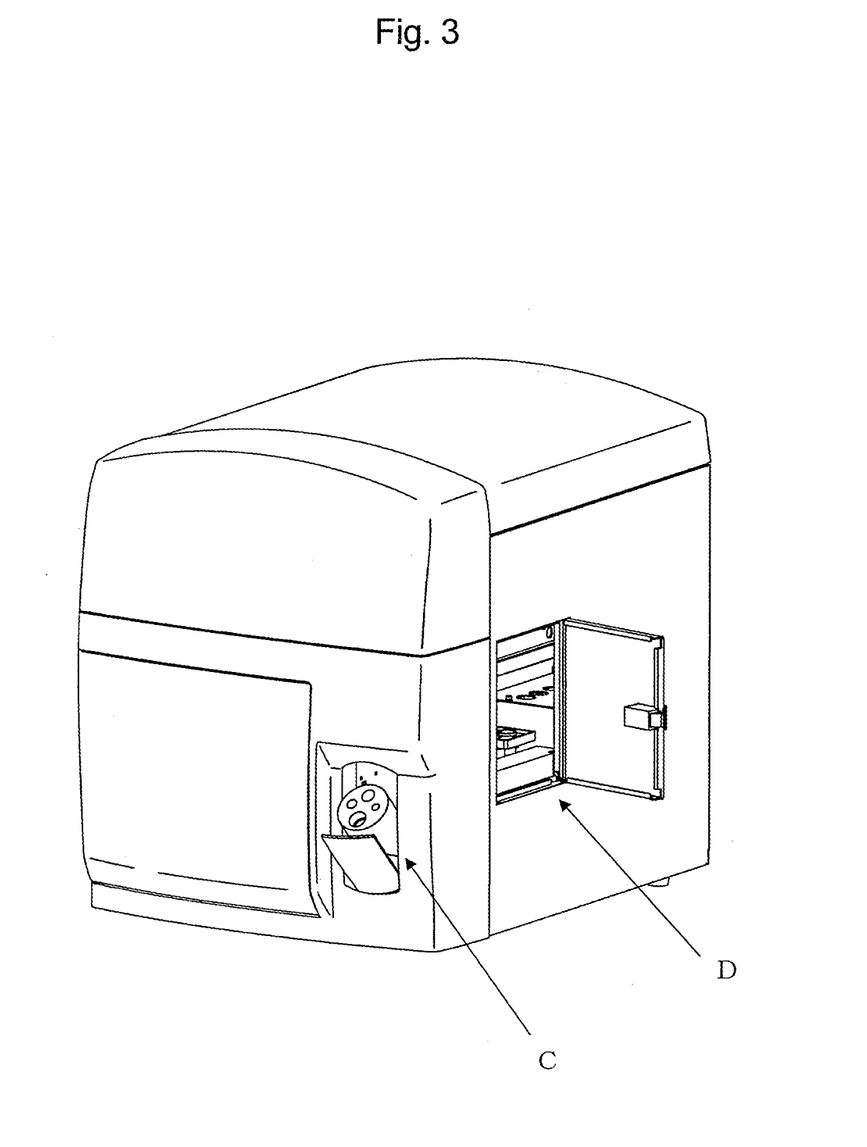
FIG. 3 shows one example of the appearance of the apparatus for measuring blood cells and immunity from whole blood of the present invention.

While the general appearance of the present apparatus for measuring blood cells and immunity from whole blood is not particularly limited, for example, one shown in FIG. 3 can be mentioned. In the embodiment of FIG. 3, a specimen container set part (blood collecting tube holder) C for setting a specimen container (also referred to as blood collecting tube) containing a specimen is openably/closably provided on the front face. In addition, door D is provided on the side face to expose a part holding the reagent containers for immunity measurement, which enables supplementation of the reagents and maintenance of the immunity measuring part.

The techniques of conventionally-known whole blood cell immunity measuring apparatuses, blood cell counting and measuring apparatuses and immunity measuring apparatuses such as the above-mentioned patent document 1 and the like may be referred to for the basic configuration, mechanism, control, and measurement techniques necessary for placing the immunity measuring part and the blood cell counting-measuring part at predetermined positions, moving the sampling nozzle in a controlled manner, performing suction and discharge of specimens and reagents, and further, automatically performing immunity measurement and blood cell counting and measuring in each cell. As a control part for controlling the mechanism of each part and processing the obtained data, a computer is appropriate.

The immunity measurement to be performed by the present apparatus only needs to be an immunological measurement such as the analysis of components in blood plasma and the like, and is not particularly limited. Particularly, the measurement of CRP values is frequently used as a representative inflammation marker in clinical laboratory tests (bacterial infection etc.), and is an important measurement item for an apparatus for measuring blood cells and immunity from whole blood.

In the following explanation, the present invention is explained by referring to CRP measurement as an actual example of immunity measurement.

[Immunity Measuring Part (CRP Measuring Part)]

In the embodiment shown in FIG. 1, an immunity-measuring cell 19 is a cell configured to be able to measure CRP, which is provided with a light-irradiation part 19a and a light detection part 19b for the CRP measurement at the lower wall surfaces of the cell, and configured to be able to appropriately stir the liquid contained inside. In the following, the immunity-measuring cell is also referred to as the CRP cell.

In the CRP cell, the prior art may be referred to for the technique of optically measuring CRP according to the latex coagulating method, arrangement and structures of the elements in the light-irradiation part and the light detection part, material of the cell, and the configuration of the cell suitable for the measurement of CRP such as the shape, size and the like thereof. In FIG. 1, a configuration containing a light-irradiation part 19a and a light detection part 19b disposed to face each other is suggested.

An exhaust pipe shown with a broken line is connected to the lower end part of the CRP cell 19, whereby a waste liquid is delivered to a waste liquid container 18, through an electromagnetic valve 19c for pathway switching and an electromagnetic valve device 12, by pump P.

A reagent container 20 for CRP measurement contains a hemolysis reagent (hereinafter to be referred to as R1 reagent). The R1 reagent may be known and, for example, a solution thereof a surfactant (synthesized substance or natural product such as saponin) as a main component and the like can be mentioned.

A reagent container 21 contains a buffer liquid (hereinafter to be referred to as R2 reagent). The R2 reagent may also be known and, for example, Tris-HCl (Tris-hydrochloric acid) buffer liquid, glycine buffer liquid and the like can be mentioned.

A reagent container 22 contains an anti-human CRP sensitized latex immunoreagent (hereinafter to be referred to as R3 reagent). The R3 reagent only needs to be a reagent usable for CRP measurement by the latex coagulating method.

In a preferable embodiment, these reagent containers are configured to be collectively opened/closed by a lid that swings in the upward and downward directions by an actuator such as solenoid, stepping motor and the like.

In a preferable embodiment, moreover, the reagent containers 21, 22 are contained in a cooling box provided with an electronic cooler composed of a Peltier element.

[Blood Cell Counting-Measuring Part]

While the measurement items of blood cells to be performed in the blood cell counting-measuring part are not particularly limited, for example, they may be counting of red blood cells (volume and frequency distribution), measurement of hemoglobin amount, classification of white blood cells into 3 types (counting of monocyte, lymphocyte and granulocyte fractions) as in patent document 1, or classification of white blood cells into 5 types (classification and counting of lymphocytes, monocytes, neutrophils, eosinophils, and basophils) may be further performed as in the embodiment shown in FIG. 1 of the present invention. These measurement items can be appropriately determined according to the object of the apparatus, demand of the user, cost of the product and the like.

A device for counting and measuring blood cells has a configuration to be operated by a control part, in each blood cell counting-measuring cell, which is necessary for performing the electric resistance method (also called an impedance method) and the optical measurement method according to the measurement items.

For example, WBC (number of white blood cells), RBC (number of red blood cells), PLT (number of platelets), MCV (volume of red blood cells), and Hct (hematocrit value) are measured by the electric resistance method as in the apparatus of patent document 1, and Hgb (hemoglobin concentration) and the like may be measured by absorption spectrophotometry in the cyanmethemoglobin method.

In the apparatus of patent document 1, the WBC/Hgb blood cell counting-measuring cell contains a measurement electrode pair for measuring WBC based on the electric resistance method and a light-irradiation part and a light-receiving part for measuring Hgb. The RBC/PLT blood cell counting-measuring cell contains a measurement electrode pair for measuring RBC and PLT based on the electric resistance method.

In the embodiment shown in FIG. 1 of the present invention, the blood cell counting-measuring cells provided as blood cell counting-measuring parts are BASO cell 27a, LMNE cell 27b, RBC cell 27c, and WBC cell 27d.

BASO cell 27a is a cell for counting basophils, wherein components other than basophils are hemolyzed or contracted by a hemolysis agent to leave only the basophils to be counted, and the basophils are counted by the electric resistance method using an aperture and electrodes.

LMNE cell 27b is a cell configured to count lymphocytes (L), monocytes (M), neutrophils (N), and eosinophils (E) by the below-mentioned light-focused flow impedance method.

RBC cell 27c is a cell configured to count red blood cells and platelets and, like the RBC/PLT blood cell counting-measuring cell in the apparatus of patent document 1, an aperture and electrodes are provided on the lower part of the cell so that the electric resistance method can be performed.

WBC cell 27d is similar to the WBC/Hgb blood cell counting-measuring cell in the apparatus of patent document 1, and provided to more accurately count white blood cells. In this cell, the hemoglobin concentration is also measured besides counting the white blood cells.

In an electrical resistance method, a sample liquid made of a blood specimen dispersed in a diluting liquid is introduced into a flow channel provided with an aperture (small opening) like an orifice, which has a reduced cross-sectional area, and an aperture is interposed between a pair of electrodes, and the volume of a particle passing through the aperture is measured based on the changes of the electrical characteristics between the electrodes.

On the other hand, a preferable optical technique for identifying a blood cell is flow cytometry. According to this technique, a predetermined irradiation light is irradiated as a beam light focused on the blood cells in a sample liquid advancing through a flow channel, and the blood cells are distinguished from optical characteristics such as light scattering, light absorbance and the like resulting therefrom.

A method involving flow cytometry and the electric resistance method to be performed at the same time (light-focused flow impedance method) is a preferable method for classifying white blood cells into 4 types (obtaining a LMNE matrix). In the embodiment of the present invention, a flow channel for the light-focused flow impedance method, and a light irradiating device, a light receiving device and an electrodes pair therefor are provided in the LMNE cell 27b, whereby the data for classifying white blood cells into 4 types (data pairs for each blood cell [volume, absorbance]) can be obtained.

The count results of blood cells are appropriately processed in the control part, and displayed as a scattergram such as a LMNE matrix, or a histogram and the like.

The conventionally-known techniques may be referred to for each device configuration necessary for performing the electric resistance method, flow cytometry, and light-focused flow impedance method.

[Sampling Nozzle and Driving Mechanism Therefor]

In the embodiment shown in FIG. 1, a specimen container 4, reagent containers 20, 22, 21, CRP cell 19, cleaning chamber A for immunity measurement, and blood cell counting-measuring cells (27a, 27b, 27c, 27d) are placed at predetermined positions. By this arrangement, a sampling nozzle (hereinafter to be also referred to as "nozzle") moves to each predetermined position as well as downwardly and upwardly, thus enabling suction and discharge of the specimen and reagents. Since the moving route of the nozzle and the mechanism of the probe unit are not complicated, and rapid processing is possible, respective predetermined positions that are preferably aligned and placed in one line as in FIG. 4(*b*) are preferable.

A nozzle is also called a needle, and is a long and thin pipe used for suction and discharge of specimens and reagents by inserting the tip thereof into each container and cell. The back-end of a nozzle is connected by piping to a sucking-discharging pump via an electromagnetic valve.

The conventionally-known techniques such as patent document 1 and the like may be referred to for the mechanism of a probe unit 13, which horizontally moves the nozzle along a predetermined pathway, as well as downwardly and upwardly. Examples thereof include a rectilinear mechanism using a timing-belt (or V-belt), which has a shape of an endless belt (looped belt) and the like, a rectilinear mechanism by a ball screw, a rectilinear mechanism by a cylinder, a rectilinear mechanism by other actuator, a moving mechanism by a driving arm, which is a combination of these, and the like.

In the embodiment shown in FIG. 1, the nozzle can move in the horizontal direction and the vertical direction in the same manner as in FIG. 4(*a*), by the timing belt 31 in the horizontal direction and the timing belt 37 for the upward and downward directions.

The nozzle reciprocates almost right above the reagent containers and cells aligned and placed on a straight line, and descends or ascends at predetermined positions to perform sucking and discharge of specimens and reagents, and cleaning. Such movements are controlled by a computer and performed as programmed.

A nozzle cleaning device 39 accompanies the nozzle 36.

The nozzle cleaning device has an annular-shaped main part, and the nozzle passes through the central through-hole thereof (the tip of the nozzle is located below the nozzle cleaning device).

The nozzle cleaning device 39 moves in the horizontal direction along with nozzle 36, and fixed at a certain height in the vertical direction. Therefore, when nozzle 36 moves downwardly and upwardly, the annular-shaped main part of the nozzle cleaning device 39 relatively moves on the outer surface of the nozzle.

In a preferable embodiment, when the nozzle moves to the lowest part, a diluting liquid is discharged from the annular-shaped main part of the nozzle cleaning device, whereby the whole outer peripheral surface of the nozzle is washed.

[Cleaning Chamber for Immunity Measurement]

The cleaning chamber for immunity measurement may be any as long as it has a depth sufficient to receive the part of the nozzle to be immersed in the reagent and the like. While such depth varies depending on the nozzle, for example, it is preferably about 20 mm-80 mm.

The shape of the body of the cleaning chamber for immunity measurement is not particularly limited. However, a cylindrical shape is preferable since the liquid injected into the chamber does not remain but is completely discharged (from the aspect of liquid waste efficiency). When the body of the cleaning chamber for immunity measurement has a cylindrical shape, the inner diameter thereof is not particularly limited, and preferably about 10 mm-20 mm. When the inner diameter of the cleaning chamber for immunity measurement is excessively large, the consumption amount of the cleaning liquid becomes high, and a longer time is necessary for filling the chamber with a diluting liquid and the like for cleaning to a predetermined level. Also, it is disadvantageous for the miniaturization of the apparatus and the like.

On the other hand, when the inner diameter is excessively small, a carriage (moving mechanism such as belt and the like) used for moving the nozzle in the horizontal direction is requested to have high accuracy of the stop position, which in turn unpreferably increases the risk of damaging the nozzle and the cleaning chamber, and scattering of the diluting liquid due to a failure of the nozzle to descend into the chamber.

The material of the cleaning chamber for immunity measurement may be any as long as it has chemical resistance and processability and, for example, polyvinyl chloride (PVC), polyethylene terephthalate (PET), polypropylene (PP) and the like can be mentioned. In view of cost and processability, PVC is a preferable material.

As shown in FIG. 1, the position of the cleaning chamber for immunity measurement is preferably next to the immunity-measuring cell (CRP cell) and between the blood cell counting-measuring cell and the immunity-measuring cell, since the movement of the nozzle can be minimized.

As shown in FIG. 1 with a broken line, an exhaust pipe similar to that in the CRP cell is connected to a lower end part of the cleaning chamber for immunity measurement, whereby the waste liquid is transferred to a waste liquid container 18 via an electromagnetic valve device 12 and a pump P.

The step of the final cleaning of the nozzle in the cleaning chamber for immunity measurement is the same as the cleaning conventionally performed in the CRP cell. To be specific, a predetermined amount of a clean diluting liquid is discharged in the chamber, and the sucking and discharging of the diluting liquid is repeated (preferably about 2 or 3 repeats) to clean the inner surface of the nozzle. Where necessary, the diluting liquid used needs to be discarded and fresh diluting liquid needs to be supplied to repeat the discharging and sucking. In a preferable embodiment, the diluting liquid is discarded once or twice. In this case, a nozzle cleaning device may be activated.

In addition, the nozzle after sucking reagents R1-R3 may be cleaned in the cleaning chamber for immunity measurement.

The cleaning in the present invention may be an operation to dilute and wash out a substance adhered to the surface of a target object with a diluting liquid alone or, where necessary, an operation to remove a substance adhered to the surface of a target object with a diluting liquid and a cleaning agent.

The diluting liquid may be any as long as it can be used for diluting a specimen for the measurement, such as physiological saline, phosphate buffer diluting liquid and the like. In the present invention, the diluting liquid is also used for cleaning.

The cleaning of the outer surface of a nozzle by a nozzle cleaning device, and the final cleaning of the nozzle in a cleaning chamber for immunity measurement may be performed using a diluting liquid alone.

The cleaning chamber for immunity measurement may be used, in addition to the final cleaning of the nozzle, as a receiving port for cleaning the outer surface of the nozzle by a nozzle cleaning device in the step of dispensing each reagent in the CRP cell. In other words, in the step for dispensing each reagent for immunity measurement, the nozzle may be moved to be right over the cleaning chamber for immunity measurement, and the nozzle cleaning device may be activated thereon.

Using the aforementioned configuration including a cleaning chamber for immunity measurement, the operating time can be advantageously shortened by parallel operation of the chamber drainage and reduction of the carriage travel distance.

[Specimen Cleaning Chamber]

In a preferable embodiment of the present invention, specimen cleaning chamber B is further provided as shown in FIG. 1. The specimen cleaning chamber exclusively cleans a nozzle after dispensation for counting and measuring the blood cells, which possibly has blood thereon.

The shape, size and material of the specimen cleaning chamber may be similar to those of the above-mentioned cleaning chamber for immunity measurement. A discharge pipe is connected to a lower end part of the specimen cleaning chamber, as shown in FIG. 1 with a broken line, whereby the waste liquid is transferred to a waste liquid container 18 via an electromagnetic valve device 12 and a pump P.

As shown in FIG. 1, by using the cleaning chamber for immunity measurement and the specimen cleaning chamber for different purposes, cleaning the nozzle free of possibility of blood adhesion in the cleaning chamber for immunity measurement, and cleaning the nozzle possibly having blood adhered thereon in the specimen cleaning chamber, the contamination between specimens can be prevented more completely, and the processing time for one specimen can be advantageously shortened by employing the parallel and simultaneous operation.

Figure 2:
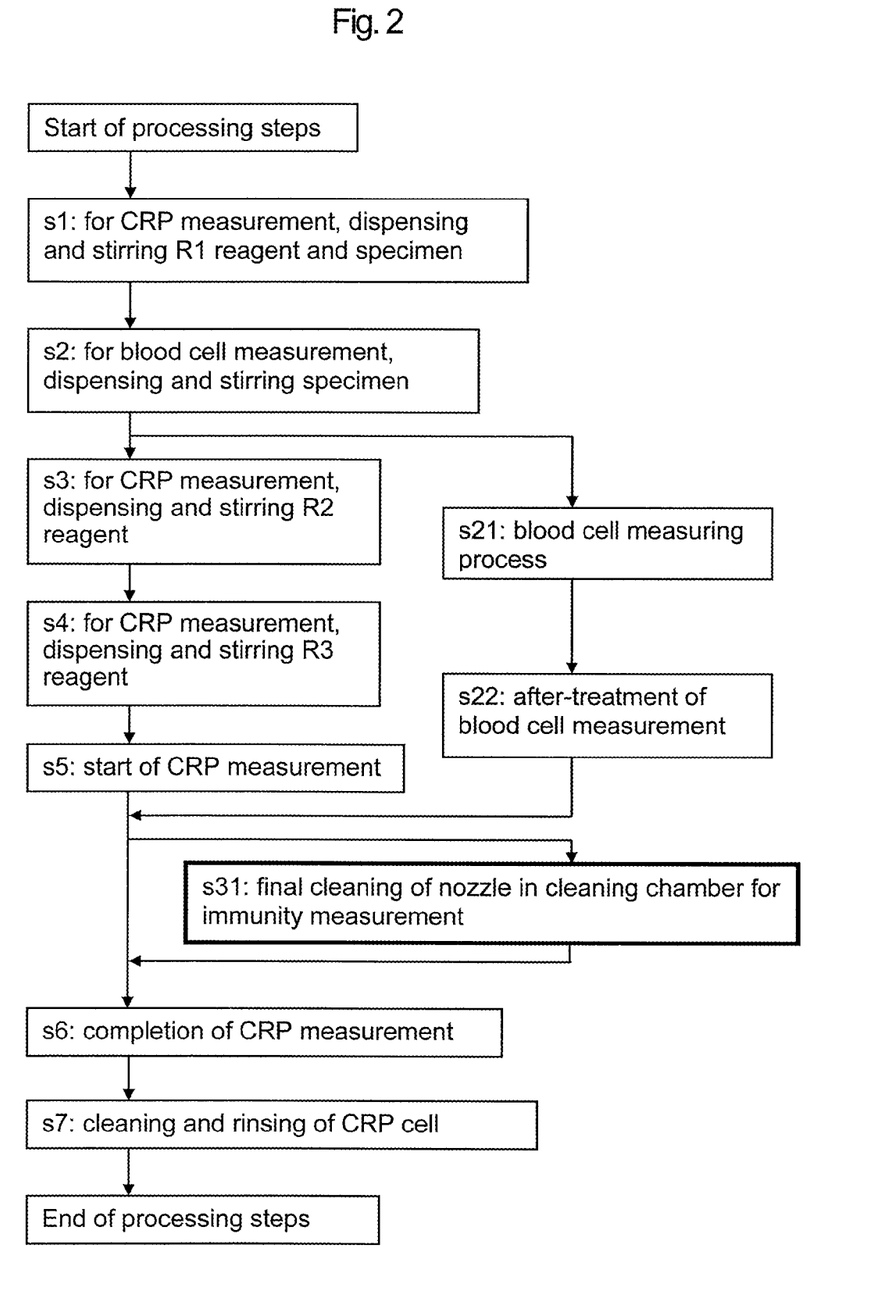
FIG. 2 is a flow chart showing the movement of the sampling nozzle in the apparatus for measuring blood cells and immunity from whole blood of the present invention.

FIG. 2 is a flowchart showing one example of the sequential operation for cleaning the nozzle by cleaning chamber A for immunity measurement and specimen cleaning chamber B shown in FIG. 1.

The operation of each part of the apparatus involves, according to the commands previously determined by the control part (computer), moving the nozzle horizontally and vertically by a probe unit, and suction and discharge performed by an electromagnetic valve part. In the following explanation, except for important movements, the nozzle behavior is described without detailed movements such as [upwardly moving from a certain position, horizontally moving, and downwardly moving to reach the next position] and the like, and simply expressed by [moving from a certain position to the next position].

First, when the processing step is started by turning on a start switch by a user, the nozzle starts the motion of step s1. The turning on operation of the start switch may be performed by any manner such as pressing a push button, a remote operation by communication with another computer and the like. For example, the operation of closing the lid of the specimen container set part C in FIG. 3 may also execute start switch ON.

(Step s1)

First, the nozzle 36 in the home position is activated to perform CRP measurement, moves to the R1 reagent container 20 and sucks R1 reagent.

After the suction, the nozzle moves to be above the cleaning chamber A for immunity measurement, and the outer surface thereof is cleaned by the nozzle cleaning device (the nozzle descends and ascends for cleaning).

Then, the nozzle moves to the specimen container 4, and sucks the specimen (whole blood) in the specimen container 4 for the CRP measurement.

Then, the nozzle moves to the specimen cleaning chamber B, and the outer surface thereof is cleaned by the nozzle cleaning device (the nozzle descends and ascends for cleaning).

Then, the nozzle moves to the CRP cell, and discharges the sucked specimen and the R1 reagent into the CRP cell. Thereafter, the liquid in the CRP cell is stirred by being repeatedly drawn and extruded by a quantitative discharging device (CRP syringe) 19d exemplarily shown as a preferable embodiment in FIG. 1.

Then, the nozzle moves to the specimen cleaning chamber B, and the inner surface and the outer surface of the nozzle are cleaned by the nozzle cleaning device.

(Step s2)

The nozzle moves to the specimen container 4 for counting and sucking the specimen (whole blood) in the specimen container 4 for counting-measuring the blood cells.

Then, the nozzle moves to the specimen cleaning chamber B, and the outer surface of the nozzle is cleaned by the nozzle cleaning device.

Then, the nozzle moves to the WBC cell 27d, and dispenses the sucked specimen into the cell. At the same time, a diluting liquid is injected into the cell from the piping (not shown) connected to the side surface of the cell, and air is discharged by a pump (not shown) from the piping (not shown), which is connected to the lower part of the cell, to stir the inside of the cell.

Then, the nozzle moves to the BASO cell 27a, and dispenses the sucked specimen into the cell. At the same time, a basophil hemolysis agent is injected into the cell from the piping (not shown) connected to the side face of the cell, and air is discharged by a pump (not shown) from the piping (not shown), which is connected to the lower part of the cell, to stir the inside of the cell.

Then, the nozzle moves to the LMNE cell 27b, and dispenses the sucked specimen into the cell. At the same time, an eosinophil measurement reagent is injected into the cell from the piping (not shown) connected to the side face of the cell, and air is discharged by a pump (not shown) from the piping (not shown), which is connected to the lower part of the cell, to stir the inside of the cell.

Then, the nozzle moves to the specimen cleaning chamber B, and the inner surface and outer surface of the nozzle are cleaned by the nozzle cleaning device.

A part of the specimen liquid diluted in the WBC cell 27d in the above-mentioned step s2 is transferred to the RBC cell 27c, the diluting liquid is injected into the cell from the piping (not shown) connected to the RBC cell and, in the same manner as above, air is discharged to stir the inside of the cell, whereby the dilution is completed. Thereafter, a hemoglobin hemolysis reagent is injected into the WBC cell and, in the same manner as above, air is discharged to stir the inside of the cell, whereby the specimen is lysed. In addition, the diluting agent is injected into the LMNE cell from the piping (not shown) connected to the cell and, in the same manner as above, air is discharged to stir the inside of the cell, whereby the dilution is completed.

(Step s21)

In the BASO cell 27a, a specimen liquid passes through a device for performing the electric resistance method, which is formed on the lower part, whereby basophils are counted.

In the LMNE cell 27b, a specimen liquid passes through a device for performing a light-focused flow impedance method, which is formed on the lower part, whereby each volume and each absorbance of lymphocyte (L), monocyte (M), neutrophil (N) and eosinophil (E) are measured. The measurement data are transmitted to the control part, and processed for counting-measuring the cells for the classification into 4 types by the LMNE matrix and the like.

In the RBC cell 27c, a specimen liquid passes through the device for the electric resistance method, which is formed on the lower part, whereby the red blood cells and platelets are measured for the number and volume.

In the WBC cell 27d, the hemoglobin concentration is measured by an optical device for measuring the absorbance by colorimetry (non-cyanogen method). In addition, a specimen passes through the device for performing the electric resistance method, which is formed on the lower part, and the number of white blood cells is measured. The measurement data are transmitted to the control part, and processed for frequency distribution.

(Step s22)

For an after-treatment of the measurement in the BASO cell 27a, the nozzle moves to the BASO cell, and a diluting liquid is injected into the cell from the nozzle cleaning device.

(Step s3)

In parallel with the treatment in step s21, the nozzle moves to the R2 reagent container for the CRP measurement, and sucks R2 reagent.

Then, the nozzle moves to be above the cleaning chamber A for immunity measurement, and the outer surface of the nozzle is cleaned by the nozzle cleaning device.

Then, the nozzle moves to the CRP cell, and discharges the sucked R2 reagent into the CRP cell.

Then, the nozzle moves to be above the cleaning chamber A for immunity measurement, and the outer surface of the nozzle is cleaned by the nozzle cleaning device.

(Step s4)

Then, the nozzle moves to the R3 reagent container for the CRP measurement, and sucks R3 reagent.

Then, the nozzle moves to be above the cleaning chamber A for immunity measurement, and the outer surface of the nozzle is cleaned by the nozzle cleaning device.

Then, the nozzle moves to the CRP cell, and discharges the sucked R3 reagent into the CRP cell.

Then, the nozzle moves to be above the cleaning chamber A for immunity measurement so as to be cleaned in step s31 mentioned below.

(Step s5)

The CRP measurement in the CRP cell is started. The processing time until completion of the measurement is about 60 seconds.

(Step s31)

When the CRP measurement in the CRP cell is started, the nozzle moves to the inside of the cleaning chamber A for immunity measurement, and the inner surface and outer surface of the nozzle are sufficiently cleaned with a diluting liquid. In this step, discharging the diluting liquid, sucking and discharging the same into the cleaning chamber A for immunity measurement is repeated. Where necessary, the diluting liquid is discarded, and a fresh diluting liquid is used to repeat discharging, sucking and discharging again of the diluting liquid.

(Step s6)-(Step s7)—Completion of Processing Steps

When the final cleaning of the nozzle is completed and the CRP measurement in step s6 is completed, the nozzle moves to the CRP cell. At step s7, a cleaning solution is injected into the CRP cell, the cleaning solution is brought into contact with the inner surface of the CRP cell for about 1 or 2 seconds, and then the cell is rinsed with the diluting liquid, and the processing steps are completed.

The contact of the cleaning solution with the inner surface of the CRP cell is an effective processing step to extend the interval between routine cleanings (requiring about minutes for cleaning once), for which the measurement is stopped to remove latex particles deposited on the inner surface of the CRP cell.

In the present invention, a cleaning chamber for immunity measurement is newly provided, a specimen cleaning chamber is further provided, and they are controlled to be used completely differently depending on the presence or absence of blood attached thereto, as explained above by referring to the flowchart of FIG. 2. Therefore, the cleaning chamber for immunity measurement has a sufficiently small possibility of contamination with blood. Moreover, the final cleaning of the nozzle, which takes a sufficiently long time in the cleaning chamber for immunity measurement, does not influence the whole processing steps.

INDUSTRIAL APPLICABILITY

The present invention can drastically shorten the measurement processing time necessary for one specimen while maintaining all conventional processing steps, by performing a parallel and simultaneous processing of the final cleaning of the nozzle by a newly-formed cleaning chamber for immunity measurement. Consequently, a preferable apparatus for measuring blood cells and immunity from whole blood can be provided to medical institutions where a large number of specimens are measured.

This application is based on patent application No. 2013-093773 filed in Japan, the contents of which are incorporated in full herein.

The invention claimed is:

1. An apparatus for measuring blood cells and immunity from whole blood, comprising:
    an immunity measuring part comprising an immunity measuring cell;
    reagent container(s) containing reagent(s) for the immunity measurement; and
    a blood cell counting-measuring part comprising blood cell counting-measuring cell(s);
    wherein the immunity measuring part, the reagent container(s) and the blood cell counting-measuring part are placed at predetermined positions, and
    a controller configured to control such that
    a single sampling nozzle moves to the predetermined positions and moves downwardly and upwardly to suck and discharge a specimen and the reagent(s), and
    an immunity measurement in the immunity measuring cell and counting and measuring of the blood cells in the blood cell counting-measuring cell(s) are performed,
    the apparatus further comprising:
        a first cleaning chamber for blood cell count-measurement, which is for cleaning the sampling nozzle, the sampling nozzle being in a state possibly having blood thereon after dispensing for counting and measurement of the blood cells; and
        a second cleaning chamber for immunity measurement, which is different from the first cleaning chamber, and is a separate and dedicated cleaning chamber for immunity measurement exclusively for finally cleaning the sampling nozzle after completion of dispensing the specimen and the reagent(s) to the immunity measuring cell(s),
    wherein the controller is configured to control such that a diluting liquid or a diluting liquid containing a cleaning agent fills the second cleaning chamber to a predetermined level and is discarded therefrom;
    the controller is configured to control such that the sampling nozzle is immersed in the diluting liquid or the diluting liquid containing the cleaning agent, and an outer surface and an inner surface of the sampling nozzle are cleaned in the second cleaning chamber for immunity measurement, by an operation of the sampling nozzle including sucking and discharging the diluting liquid supplied in the second cleaning chamber or the diluting liquid containing the cleaning agent supplied in the second cleaning chamber, while the immunity measurement in the immunity measuring cell is performed, and
    the controller is configured to control such that cleaning of the sampling nozzle immediately after use for immunity measurement is not performed in the first cleaning chamber, and cleaning of the sampling nozzle immediately after use for blood cell count-measurement is not performed in the second cleaning chamber.

2. The apparatus for measuring blood cells and immunity of whole blood according to claim 1, wherein the first cleaning chamber is different from the blood cell counting-measuring cell(s).

3. The apparatus for measuring blood cells and immunity from whole blood according to claim 1, further comprising:
    a sampling nozzle cleaning device accompanying the sampling nozzle, which is configured to clean the outer surface of the nozzle with a diluting liquid; and
    a control configuration such that, in a step for dispensing reagent(s) for immunity measurement to the immunity measuring cell, the outer surface of the sampling nozzle is cleaned by the sampling nozzle cleaning device utilizing the second cleaning chamber for immunity measurement.

4. The apparatus for measuring blood cells and immunity of whole blood according to claim 3, wherein the first cleaning chamber is different from the blood cell counting-measuring cell(s).

\* \* \* \* \*